United States Patent [19]

Okada et al.

[11] Patent Number: 5,276,179
[45] Date of Patent: Jan. 4, 1994

[54] SULFONAMIDE DERIVATIVE

[75] Inventors: Hisashi Okada; Morio Yagihara, both of Minami-ashigara, Japan

[73] Assignee: Fuji Photo Film Co., Ltd., Kanagawa, Japan

[21] Appl. No.: 811,138

[22] Filed: Dec. 20, 1991

[30] Foreign Application Priority Data

Dec. 21, 1990 [JP] Japan .................. 2-404797

[51] Int. Cl.$^5$ .......................... C07C 315/00
[52] U.S. Cl. .................................. 562/556
[58] Field of Search ......................... 562/556

[56] References Cited

U.S. PATENT DOCUMENTS

| | | | |
|---|---|---|---|
| 3,721,706 | 3/1973 | Hoffman | 562/556 |
| 4,222,777 | 9/1980 | Nakajima | 430/363 |
| 4,536,298 | 8/1985 | Kamei | 562/556 |

FOREIGN PATENT DOCUMENTS

| | | | |
|---|---|---|---|
| 1277970 | 10/1961 | France | 562/556 |
| 58-201752 | 11/1983 | Japan | |
| 59-46252 | 3/1984 | Japan | |
| 61-100266 | 5/1986 | Japan | |

OTHER PUBLICATIONS

Martell, "Chemistry of the Metal Chelate Compounds," pp. 471–513 (1952).
"Hackh's Chemical Dictionary," 4th Ed., p. 27 (1969).

*Primary Examiner*—Michael L. Shippen
*Attorney, Agent, or Firm*—Sughrue, Mion, Zinn, Macpeak & Seas

[57] ABSTRACT

The sulfonamide derivative according to the present invention is expressed by a general formula:

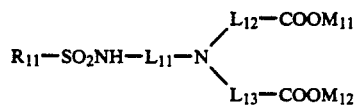

(where $R_{11}$ represents an alkyl group having 5 or less carbon atoms; Each of $L_{11}$, $L_{12}$ and $L_{13}$ represents an alkylene group; Each of $M_{11}$ and $M_{12}$ represents a hydrogen atom or a cation.)

This compound is suitable for the applications such as photographic processing solution, for chelate titration or analytical reagent for medical treatment or for medical drugs as a metallic ion shielding agent.

7 Claims, No Drawings

SULFONAMIDE DERIVATIVE

BACKGROUND OF THE INVENTION

The present invention relates to a new sulfonamide derivative useful as a metal ion shielding agent.

As a compound of this type, a sulfonamide derivative given by the following formula has been known in the past:

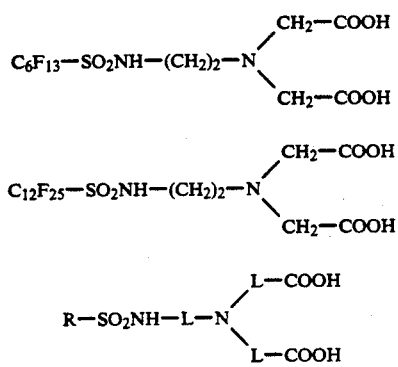

(where R represents an aromatic group, and L an alkylene group.) However, none of them is known as a metal ion shielding agent.

When it is attempted to use the compound as a metal ion shielding agent, solubility to water is low, and deposition occurs when the compound is used or it is used as a chelate of metal. This causes problems, for example, when the compound is used as a metal ion shielding agent for photographic processing solution, for chelate titration or for analytical reagents for medical treatment or for medical drugs.

It is an object of the present invention to provide a new sulfonamide derivative useful as a metal ion shielding agent.

SUMMARY OF THE INVENTION

The present invention relates to a new sulfonamide derivative, and in particular to a new sulfonamide derivative given by the following general formula (A): General formula (A)

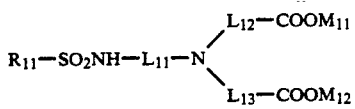

In the formula, $R_{11}$ represents an alkyl group having 5 or less carbon atoms. Each of $L_{11}$, $L_{12}$ and $L_{13}$ represents an alkylene group. Each of $M_{11}$ and $M_{12}$ represents a hydrogen atom or a cation.

The compound expressed by the above general formula (A) according to the present invention is soluble in water and is suitable for the applications such as photographic processing solution, chelate titration or analytical reagents for medical treatment, or medical drugs as a metal ion shielding agent.

The above and other objects, features and advantages of the present invention will become apparent from the following description, in which preferred embodiments of the present invention are shown by way of illustrative examples.

DESCRIPTION OF THE PREFERRED EMBODIMENTS

In the general formula (A), the alkyl group given by $R_{11}$ may be in form of a straight chain, a branched chain or a ring, such as methyl group, ethyl group, n-propyl group, i-propyl group, n-butyl group, i-butyl group, t-butyl group, n-pentyl group, i-pentyl group, t-pentyl group, cyclopentyl group, etc.

$R_{11}$ may be provided with a substituent. As the substituent, there are, for example, alkoxy group, amino group, acylamino group, sulfonyl amino group, ureide group, urethane group, aryloxy group, sulfamoyl group, carbamoyl group, alkylthio group, arylthio group, sulfonyl group, sulfinyl group, hydroxy group, halogen atom, cyano group, sulfo group, carboxyl group, phosphono group, aryloxy carbonyl group, acyl group, alkoxycarbonyl group, acyloxy group, carbonamide group, sulfonamide group, nitro group, hydroxamic acid group, etc. As the substituent, it is preferable to use a halogen atom, or more preferably, a fluorine atom.

As an alkyl group represented by $R_{11}$, it is preferable to use a methyl group.

The alkylene group represented by $L_{11}$, $L_{12}$ and $L_{13}$ may contain a substituent. As such substituent, the substituent given for R can be cited.

Preferably, each of $L_{11}$, $L_{12}$ and $L_{13}$ is an alkylene group in form of a straight chain, a branched chain or a ring, having 1 to 3 carbon atoms. For example, methylene group, ethylene group, trimethylene group, propylene group, etc. may be cited. More preferably, methylene group or ethylene group may be used.

As a cation given by $M_{11}$ and $M_{12}$, there are alkali metal (such as Li, Na, K), ammonium (such as ammonium, triethyl ammonium).

Concrete examples of the compounds given by the general formula (A) of the present invention include but not limited to the following compounds (compounds 1 to 6).

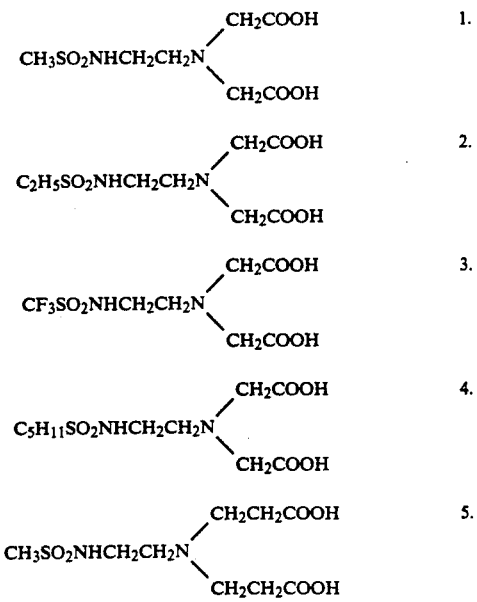

-continued

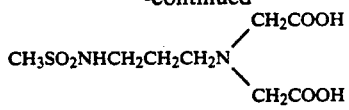

The compounds given by the above general formula (A) can be synthesized, for example, by the following method:

Specifically, the compound can be synthesized by reacting a sulfonamide substituent with an alkane with leaving group (e.g. 2-chloroethylmethane sulfonamide, 2-chloroethylpentane sulfonamide, 3-chloropropylmethane sulfonamide, etc.) with amine compound (e.g. iminodiacetic acid, nitrilo dipropionic acid, etc.) under the presence of a base.

Also, the compound can be synthesized by reacting a sulfonamide substituent with an alkane having carbonyl group (e.g. 2-methane sulfonamide ethanol, 3-methane sulfonamide propanal, 2-trifluoromethane sulfonamide ethanal, etc.) with amine compound (e.g. the amine compounds as described above) through hydrogenation reaction. Original materials of these compounds are already known and are readily available.

The above reaction according to the present invention is usually performed in a solvent. There is no restriction of the solvent except that it is not related to the reaction. It is preferable to use water, alcohol (lower alcohol such as methanol) to facilitate the reaction.

As an alkane having leaving group, compounds used for alkylation of amino group, such as halogen atom (e.g. chlorine, bromine, iodine, etc.), p-toluene sulfonate group, etc. can be used. As the base to be used, there are alkali or tertiary amine (such as triethylamine).

The base is used by a ratio of equimol—10 mols to the alkane, or more preferably, equimol—4 mols. When it is synthesized through hydrogenation reaction, palladium, platinum, cobalt, etc. carried by activated carbon or Raney nickel may be used as a catazlyst.

Reaction temperature is 0° to 100° C., or more preferably, 10° C. to 70° C.

Synthesis of Compound 1

35.7 g (0.30 mol) of iminodiacetic acid was dissolved in 120 ml (0.600 mol) of 5N sodium hydroxide. While stirring this solution, 47.3 g (0.30 mol) of 2-chloroethylmethane sulfonamide and 60 ml (0.300 mol) of 5N sodium hydroxide were gently dropped so that pH value of the reaction solution was kept to 10 to 11.

After dropping was completed, the solution was stirred up for 6 hours at 50° C. and it was then cooled down to room temperature, and 60.8 g (0.600 mol) of concentrated hydrochloric acid was added. The deposited solid was collected by filtration and was recrystalized with water. The resultant white solid was dried under reduced pressure, and 54.2 g (0.213 mol) of the desired compound 1 was obtained.

Yield: 71% Melting point: 230° to 232° C. (decomposed)

The result of element analysis

|  | H | C | N | S |
|---|---|---|---|---|
| Calculated value (%) | 5.55 | 33.07 | 11.02 | 12.61 |
| Measured value (%) | 5.52 | 32.78 | 11.00 | 12.77 |
| $^1$HNMR (D$_2$O) ppm |  |  |  |  |
| δ2.65 (t 2H) |  |  |  |  |
| δ2.76 (s 3H) |  |  |  |  |
| δ3.00 (t 2H) |  |  |  |  |
| δ3.19 (s 4H) |  |  |  |  |

What we claimed is:

1. A sulfonamide derivative expressed by a general formula:

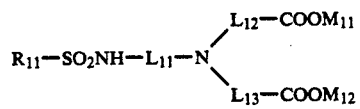

where $R_{11}$ represents a methyl group; each of $L_{11}$, $L_{12}$ and $L_{13}$ represents an alkylene group; and each of $M_{11}$ and $M_{12}$ represents a hydrogen atom or a cation.

2. A sulfonamide derivative according to claim 1, wherein each of $L_{11}$, $L_{12}$ and $L_{13}$ is an alkylene group having 1 to 3 carbon atoms.

3. A sulfonamide derivative according to claim 1, wherein $L_{11}$, $L_{12}$ and $L_{13}$ represent a methylene group or an ethylene group.

4. A sulfonamide derivative according to claim 1, expressed by a formula:

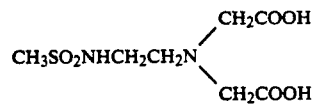

5. A sulfonamide derivative expressed by a formula:

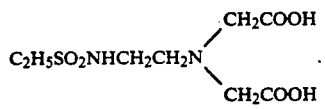

6. A sulfonamide derivative according to claim 1, expressed by a formula:

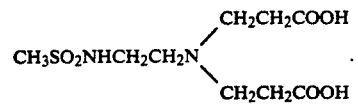

7. A sulfonamide derivative according to claim 1, expressed by a formula:

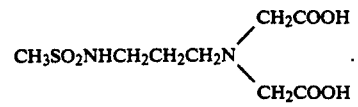

* * * * *